United States Patent [19]

Uhr et al.

[11] Patent Number: 5,077,291
[45] Date of Patent: Dec. 31, 1991

[54] FUNGICIDAL TRISUBSTITUTED 1,3,5-TRIAZINE-2,4,6-TRIONES

[75] Inventors: Hermann Uhr, Leverkusen; Alfons Adler, Cologne; Arno Widdig, Odenthal; Hermann Hagemann; Gerd Hänssler, both of Leverkusen, all of Fed. Rep. of Germany

[73] Assignee: Bayer Aktiengesellschaft, Leverkusen, Fed. Rep. of Germany

[21] Appl. No.: 585,433

[22] Filed: Sep. 20, 1990

[30] Foreign Application Priority Data

Oct. 11, 1989 [DE] Fed. Rep. of Germany ....... 3933933

[51] Int. Cl.$^5$ .................. C07D 251/34; A01N 43/66
[52] U.S. Cl. .................................. 514/241; 544/221; 544/222
[58] Field of Search ................. 544/221, 222; 514/241

[56] References Cited

FOREIGN PATENT DOCUMENTS 1670675 12/1970 Fed. Rep. of Germany .
3618662 12/1987 Fed. Rep. of Germany .
3810080 10/1989 Fed. Rep. of Germany .

OTHER PUBLICATIONS

H. Hagemann: Dikohlensaure-Derivate, p. 1022 (1983), Houben-Weyl-4th Edition.
U. Peterson: Offenketige Organo-Harnstoff, p. 352 (1983), Houben-Weyl-4th Edition.
Hagemann, Angew. Chem. 89, 789-796 (1977), pp. 789-796.
Bukac et al., Chemical Abstracts, vol. 78, entry 137104s (1973).
Eritsyan et al., Chemical Abstracts, vol. 85, entry 161525v (1976).

*Primary Examiner*—John M. Ford
*Attorney, Agent, or Firm*—Sprung Horn Kramer & Woods

[57] ABSTRACT

Fungicidal trisubstituted 1,3,5-triazine-2,4,6-triones of the formula

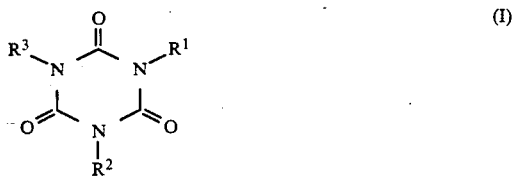

(I)

in which
R$^1$, R$^2$ and R$^3$ are different radicals and
R$^1$ represents an optionally substituted aliphatic or cycloaliphatic radical,
R$^2$ represents an optionally substituted aliphatic radical and
R$^3$ represents an optionally substituted aralkyl radical.

8 Claims, No Drawings

FUNGICIDAL TRISUBSTITUTED 1,3,5-TRIAZINE-2,4,6-TRIONES

The invention relates to new trisubstituted 1,3,5-triazine-2,4,6-triones, to processes for their preparation, and to their use for combating pests, above all as fungicides.

It has already been disclosed that 2-arylamino-4,6-dichloro-s-triazines, such as, for example, 4,6-dichloro-N-(2-chloro-phenyl)-1,3,5-triazine-2-amine, have fungicidal properties (cf. DAS (German Published Specification) 1,670,675). However, the selective fungicidal activity of these substances is only restricted to some fungi and not always sufficient.

Furthermore known as fungicides are trisubstituted 1,3,5-triazine-2,4,6-triones which in every case carry an aryl radical (cf. DE-OS 3,618,662) and also compounds which carry in each case a heterocyclically fused phenyl (cf. DE-OS (German Published Specification) 3,810,080, corresponding to U.S. Pat. No. 4,927,824).

However, the activity of these previously known compounds is not entirely satisfactory in all fields of application, in particular when low application rates and concentrations are used.

New trisubstituted 1,3,5-triazine-2,4,6-triones have been found, of the general formula (I)

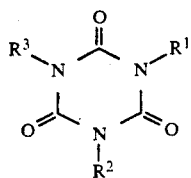

(I)

in which
  $R^1$, $R^2$ and $R^3$ are different radicals and
  $R^1$ represents an optionally substituted aliphatic or cycloaliphatic radical,
  $R^2$ represents an optionally substituted aliphatic radical and
  $R^3$ represents an optionally substituted aralkyl radical.

Furthermore, it has been found that the new trisubstituted 1,3,5-triazine-2,4,6-triones of the formula (I) in which
  $R^1$, $R^2$ and $R^3$ are different radicals and
  $R^1$ represents an optionally substituted aliphatic or cycloaliphatic radical,
  $R^2$ represents an optionally substituted aliphatic radical and
  $R^3$ represents an optionally substituted aralkyl radical,
are obtained when either
  a) 1,3-disubstituted 1,3,5-triazine-2,4,6-triones of the general formula (II)

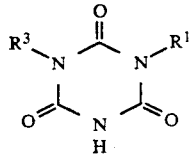

(II)

in which
  $R^1$ and $R^3$ have the abovementioned meanings, are reacted with compounds of the general formula (III)

$$R^2—X \tag{III}$$

in which
  $R^2$ has the abovementioned meaning and
  X denotes a leaving group, such as, for example, halogen, sulphate, mesylate or tosylate,
if appropriate in the presence of a diluent or solvent and if appropriate in the presence of an acid-binding agent, or when
  b) 1,3-disubstituted 1,3,5-triazine-2,4,6-triones of the general formula (IV)

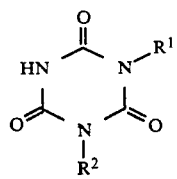

(IV)

in which
  $R^1$ and $R^2$ have the abovementioned meanings,
are reacted with compounds of the general formula (V)

$$R^3—X \tag{V}$$

in which
  $R^3$ and X have the abovementioned meanings,
if appropriate in the presence of a diluent or solvent, or when
  c) N,N'-disubstituted ureas of the general formula (VI)

$$R^1—NH—CO—NH—R^3 \tag{VI}$$

in which $R^1$ and $R^3$ have the abovementioned meanings, are reacted with a bischlorocarbonylamine of the general formula (VII)

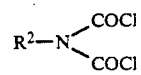

(VII)

in which $R^2$ has the abovementioned meaning, if appropriate in the presence of a diluent or solvent and if appropriate in the presence of an acid-binding agent, or when
  d) N,N'-disubstituted ureas of the general formula (VIII)

$$R^1—NH—CO—NH—R^2 \tag{VIII}$$

in which $R^1$ and $R^2$ have the abovementioned meanings, are reacted with compounds of the general formula (IX)

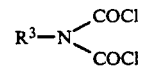

(IX)

in which $R^3$ has the abovementioned meaning, if appropriate in the presence of a diluent or solvent and if appropriate in the presence of an acid-binding agent.

Finally, it has been found that the new trisubstituted 1,3,5-triazine-2,4,6-triones of the formula (I) have very good biological properties and are suitable for combating pests, in particular fungi, and mainly for selectively combating harmful fungi in rice. It must be considered as extremely surprising that the substances according to the invention exhibit a better activity than known compounds from the prior art which have the same direction of action, and/or compounds having a similar structure.

Formula (I) provides a general definition of the trisubstituted 1,3,5-triazine-2,4,6-triones according to the invention. Preferred compounds of the formula (I) are those in which $R^1$, $R^2$ and $R^3$ are different radicals and $R^1$ represents straight-chain or branched alkyl having 1 to 12 carbon atoms, straight-chain or branched alkenyl having 3 to 12 carbon atoms or straight-chain or branched alkinyl having 3 to 12 carbon atoms, these radicals being optionally monosubstituted to polysubstituted by identical or different substituents from the series comprising alkoxy having 1 to 4 carbon atoms, halogenoalkoxy having 1 to 3 carbon atoms and 1 to 5 identical or different halogen atoms, alkylthio having 1 to 3 carbon atoms, and halogenoalkylthio having 1 to 3 carbon atoms and 1 to 5 identical or different halogen atoms; $R^1$ furthermore represents cycloalkyl which has 3 to 8 carbon atoms and which is optionally monosubstituted to hexasubstituted by identical or different substituents from the series comprising alkyl having 1 to 4 carbon atoms, alkoxy having 1 to 3 carbon atoms, halogenoalkoxy having 1 to 3 carbon atoms and 1 to 5 identical or different halogen atoms, alkylthio having 1 to 3 carbon atoms, and halogenoalkylthio having 1 to 3 carbon atoms and 1 to 5 identical or different halogen atoms, $R^2$ represents alkyl having 1 to 10 carbon atoms, alkenyl having 3 to 10 carbon atoms, alkinyl having 3 to 10 carbon atoms, alkoxyalkyl having 1 to 3 carbon atoms each in the alkoxy moiety and the alkyl moiety, alkylthioalkyl having 1 to 3 carbon atoms each in the alkylthio moiety and the alkyl moiety, alkoxycarbonylalkyl having 1 to 3 carbon atoms in the alkoxy moiety and 2 or 3 carbon atoms in the alkyl moiety, or cyanoalkyl having 1 to 5 carbon atoms in the alkyl moiety, $R^3$ represents aralkyl having 1 to 12 carbon atoms in the straight-chain or branched alkyl moiety and 6 to 12 carbon atoms in the aryl moiety, aryl representing phenyl or naphthyl and the rings in each case being optionally monosubstituted to pentasubstituted by identical or different substituents from the series comprising halogen, alkyl having 1 to 6 carbon atoms, halogenoalkyl having 1 to 4 carbon atoms and 1 to 5 identical or different halogen atoms, alkoxy having 1 to 4 carbon atoms, halogenoalkoxy having 1 to 4 carbon atoms and 1 to 5 identical or different halogen atoms, alkylthio having 1 to 4 carbon atoms, halogenoalkylthio having 1 to 4 carbon atoms and 1 to 5 identical or different halogen atoms, monoalkylamino or dialkylamino which have optionally identical or different, straight-chain or branched alkyl radicals each having 1 to 4 carbon atoms, nitro and/or benzyloxy, or the phenyl ring can optionally carry a fused, saturated ring having 3 to 5 carbon atoms.

Compounds of the formula (I) in which $R^1$, $R^2$ and $R^3$ are different radicals and $R^1$ represents straight-chain or branched alkyl having 1 to 10 carbon atoms, straight-chain or branched alkenyl having 3 to 8 carbon atoms or straight-chain or branched alkinyl having 3 to 8 carbon atoms, these radicals being in each case optionally monosubstituted to trisubstituted by identical or different substituents from the series comprising alkoxy having 1 to 3 carbon atoms, halogenoalkoxy having 1 or 2 carbon atoms and 1 to 3 chlorine and/or fluorine atoms, alkylthio having 1 or 2 carbon atoms, and halogenoalkylthio having 1 or 2 carbon atoms and 1 to 3 chlorine and/or fluorine atoms; $R^1$ furthermore represents cycloalkyl which has 3 to 6 carbon atoms and which is optionally monosubstituted to hexasubstituted by identical or different substituents from the series comprising fluorine, chlorine, alkyl having 1 to 3 carbon atoms, alkoxy having 1 or 2 carbon atoms, halogenoalkoxy having 1 or 2 carbon atoms and 1 to 3 chlorine and/or fluorine atoms, alkylthio having 1 or 2 carbon atoms, and halogenoalkylthio having 1 or 2 carbon atoms and 1 to 3 chlorine and/or fluorine atoms, $R^2$ represents alkyl having 1 to 8 carbon atoms, alkenyl having 3 to 8 carbon atoms, alkinyl having 3 to 8 carbon atoms, alkoxyalkyl having 1 or 2 carbon atoms in the alkoxy moiety and 1 to 3 carbon atoms in the alkyl moiety, alkylthioalkyl having 1 or 2 carbon atoms in the alkylthio moiety and 1 to 3 carbon atoms in the alkyl moiety, alkoxycarbonylalkyl having 1 or 2 carbon atoms in the alkoxy moiety and 2 or 3 carbon atoms in the alkyl moiety, or cyanoalkyl having 1 to 3 carbon atoms in the alkyl moiety, and $R^3$ represents aralkyl having 1 to 9 carbon atoms in the straight-chain or branched alkyl moiety and aryl represents phenyl or naphthyl, each of which can optionally be monosubstituted to tetrasubstituted by identical or different substituents from the series comprising fluorine, chlorine, bromine, alkyl having 1 to 5 carbon atoms, halogenoalkyl having 1 or 2 carbon atoms and 1 to 5 chlorine and/or fluorine atoms, alkoxy having 1 to 3 carbon atoms, halogenoalkoxy having 1 or 2 carbon atoms and 1 to 5 chlorine and/or fluorine atoms, alkylthio having 1 or 2 carbon atoms, halogenoalkylthio having 1 or 2 carbon atoms and 1 to 5 chlorine and/or fluorine atoms, dialkylamino having identical or different, straight-chain or branched alkyl radicals each having 1 to 3 carbon atoms, nitro and/or benzyloxy, or the phenyl ring contains a tri- or tetramethylene chain in the 1,2-position, must be particularly emphasized.

Compounds of the formula (I) in which $R^1$, $R^2$ and $R^3$ are different radicals and $R^1$ represents straight-chain or branched alkyl having 1 to 8 carbon atoms, straight-chain or branched alkenyl having 3 to 6 carbon atoms or straight-chain or branched alkinyl having 3 to 6 carbon atoms, it being possible for these radicals to be monosubstituted to trisubstituted by identical or different substitutents from the series comprising alkoxy having 1 or 2 carbon atoms, or alkylthio having 1 or 2 carbon atoms; or $R^1$ furthermore represents cycloalkyl which has 3 to 6 carbon atoms and which can optionally be monosubstituted to trisubstituted by identical or different substituents from the series comprising fluorine, chlorine, methyl, ethyl, methoxy, ethoxy, methylthio, ethylthio and trifluoromethyl, $R^2$ represents methyl, ethyl, propyl, n-, sec.-, iso-, tert.-butyl, n-pentyl, iso-pentyl, neo-pentyl, tert.-pentyl, allyl, 2-butenyl, propargyl, 2-butinyl, methoxymethyl, ethoxymethyl, methylthiomethyl, methoxycarbonylmethyl, ethoxycarbonylmethyl, methoxycarbonylethyl, cyanomethyl or cyanoethyl, and represents aralkyl having 1 to 7 carbon atoms in the straight-chain or branched alkyl radical and aryl represents phenyl or naphthyl each of which can be monosubstituted to trisubstituted by identical or different substituents from the series comprising fluorine, chlorine, alkyl having 1 to 4 carbon atoms, halogenoalkyl having 1 or 2 carbon atoms and 1 to 5 chlorine and/or fluorine atoms, alkoxy having 1 or 2 carbon atoms, halogenoalkoxy having 1 or 2 carbon atoms and 1 to 5 chlorine and/or fluorine atoms or benzyloxy, or the phenyl ring carries a trimethylene chain in the 1,2-position,
must be very particularly emphasized.

If, according to process a), 1-tert.-butyl-3-[2-(4-methylphenyl)-ethyl]-1,3,5-triazine-2,4,6-trione and ethyl iodide are used as starting substances, the course of the reaction can be illustrated by the following equation:

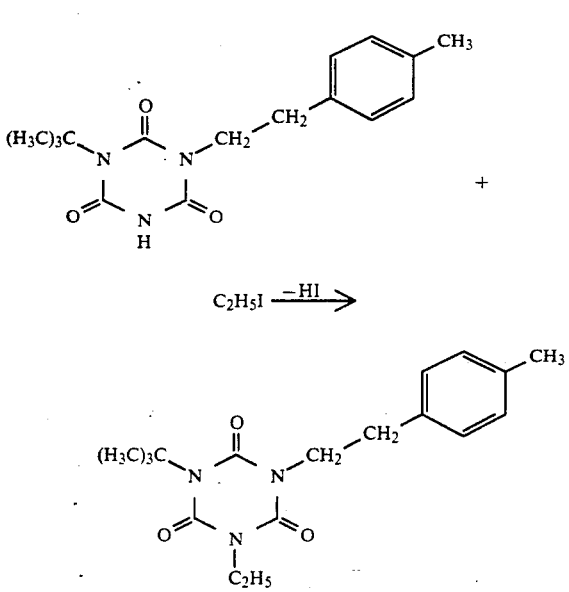

If, according to process b), 1-tert.-butyl-3-ethyl-1,3,5-triazine-2,4,6-trione and benzyl bromide are used as starting substances, the course of the reaction can be illustrated by the following reaction scheme:

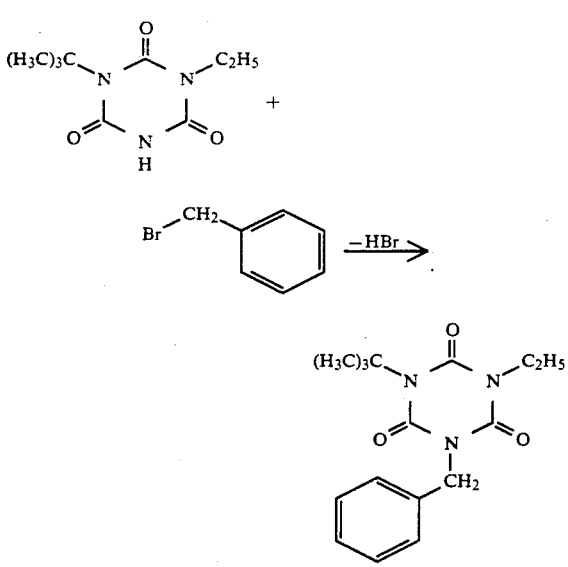

If, according to process c), N-[2-(4-methoxyphenyl)-2-(2-isopropyl)-ethyl]-N'-(neopenthyl)-urea and bis-chlorocarbonyl-N-ethylamine are used as starting substances, the course of the reaction can be illustrated by the following equation:

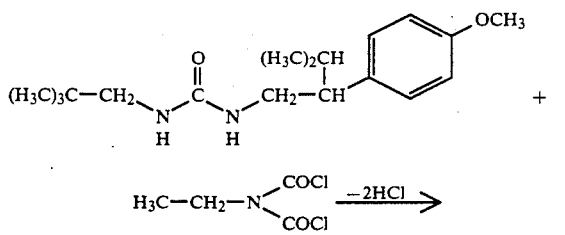

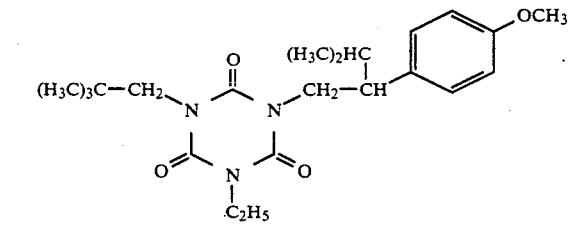

If, according to process d), bis-chlorocarbonyl-N-[2-(2,6-dichloro-phenyl)-ethylamine and N-ethyl-N'-(2,2-dimethyl-propyl)-urea are used as starting substances, the course of the reaction can be illustrated by the following equation:

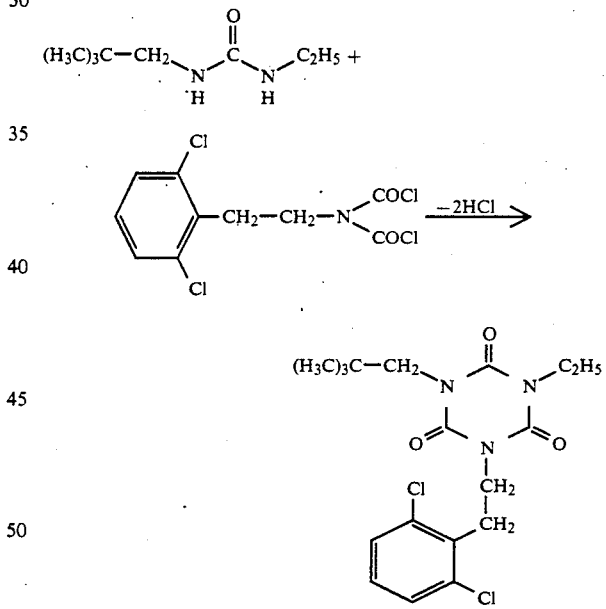

The disubstituted 1,3,5-triazine-2,4,6-triones of the general formulae (II) and (IV) which are required as starting compounds in processes a) and b) according to the invention are known in some cases and can be obtained in a manner known per se, for example from N,N'-disubstituted ureas and chlorocarbonyl isocyanate (cf. Angew. Chem. 89, 789 (1977)). The alkylating agents of the formulae (III) and (V) to be used in processes a) and b) are likewise known. In these formulae, X preferably represents chloride, bromide, iodide, sulphate, mesylate or tosylate.

The ureas of the general formulae (VI) and (VIII) to be used for processes c) and d) according to the invention are known in most cases and producible by an addition reaction of suitable isocyanates with primary amines (cf. Houben-Weyl: Methoden der organischen Chemie [Methods of Organic Chemistry], Volume E4, (1983), p. 352, Thieme-Verlag, Stuttgart).

The bis-chlorocarbonylamines of the general formula (VII) and (IX) used in processes c) and d) are likewise known (cf. Houben-Weyl: Methoden der organischen Chemie [Methods of Organic Chemistry], Volume E4, (1983), p. 1022, Thieme-Verlag, Stuttgart).

In the processes according to the invention, the reaction temperatures can be varied within a substantial temperature range. In general, processes a) and b) are carried out between 20° C. and 150° C., preferably between 50° C. and 120° C., and processes c) and d) are generally carried out between 0° C. and 150° C., preferably between 20° C. and 120° C.

When carrying out the processes according to the invention, the starting substances and, if appropriate, the acid-binding agents are employed in approximately equimolar amounts. An excess of acid-binding agents is generally not harmful.

The reactions are preferably carried out in the presence of a diluent. Suitable diluents are all inert organic solvents. These preferably include hydrocarbons, such as toluene and xylene; chlorinated hydrocarbons, such as chlorobenzene and chloroform; ketones, such as acetone; ethers, such as tetrahydrofuran and dioxane; and nitriles, such as acetonitrile.

Acid binders which can be used are all customary acid-binding agents. These preferably include tertiary amines, such as triethylamine and pyridine; alkali metal hydroxides, such as sodium hydroxide and potassium hydroxide, and alkali metal carbonates and alkali metal hydrogen carbonates, such as potassium carbonate and sodium hydrogen carbonate.

The compounds according to the invention are worked up and isolated in a customary manner. They are either obtained immediately in crystalline form, or they remain as a crystallizate or oil after the solvent has been evaporated.

The active compounds according to the invention have a powerful biological action and can be employed in practice for combating undesired pests. The active compounds are suitable for use for example as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in a customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE A (Process a) (corresponds to Example No. 38)

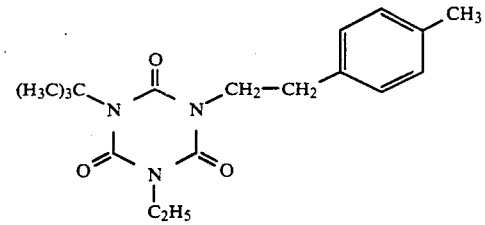

6.2 g (39.6 mmol) of ethyl iodide are added dropwise at room temperature to a solution of 10 g (33.0 mmol) of 1-tert.-butyl-3-[2-(4-methyphenyl)-ethyl]-1,3,4-triazine-2,4,6-trione and 9.1 g (66 mmol) of potassium carbonate in 50 ml of absolute acetonitrile. The reaction mixture is refluxed for 5 hours. After it has cooled, the solid constituents are separated off, and the reaction solution is transferred to cold water. The crystals which have precipitated are filtered off with suction and recrystallized from water/methanol. After drying, 9.5 g (87% of theory) of 1-tert.-butyl-5-ethyl-3-[2-(4-methylphenyl)-ethyl]-1,3,5-triazine-2,4,6-trione are obtained in the form of crystals having a melting point of 64° C.

EXAMPLE B (Process b) (corresponds to Example No. 1)

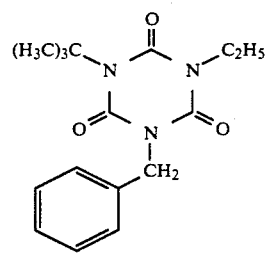

7.7 g (45 mmol) of benzyl bromide are added dropwise at room temperature to a solution of 10 g (46.9 mmol) of 1-tert.-butyl-3-ethyl-1,3,5-triazine-2,4,6-trione and 9.9 g (93 mmol) of sodium carbonate. The reaction mixture is refluxed for 6 hours. After it has cooled, the solid constituents are separated off, and the reaction solution is concentrated. The residue is taken up in methylene chloride and washed twice with water. After the organic phase has been dried over sodium sulphate, it is concentrated and distilled in vacuo. 8.5 g (60% of theory) of 5-benzyl-1-tert.-butyl-3-ethyl-1,3,5-triazine-2,4,6-trione are obtained as a highly viscous oil having a boiling point of 170° C./0.03 mbar.

EXAMPLE C (Process c) (corresponds to Example No. 53)

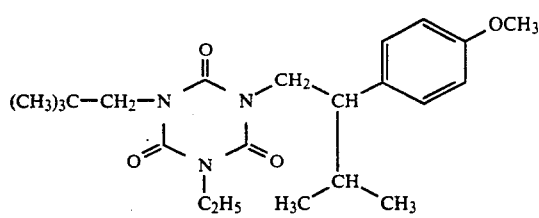

3 g (0.01 mol) of N-[2-(4-methoxy-phenyl)-2-isopropyl]-ethyl-N'-(neopentyl)-urea are dissolved in 50 ml of absolute dioxane, and 4.2 ml (0.03 mol) of triethylamine are added. A solution of 1.6 g (0.01 mol) of bis-chlorocarbonyl-N-ethylamine in 20 ml of dioxane is slowly added dropwise. The mixture is stirred for 1 hour at room temperature and then for another 15 minutes under reflux. After the mixture has been cooled, it is transferred into ice-water and extracted with methylene chloride. The methylene chloride phase is washed twice with water and then dried over sodium sulphate and evaporated.

Yield: 2.1 g = 51% of theory.

Physical data see Example 53.

The compounds of the formula (I) listed in the table below are prepared analogously to the examples given and/or the processes described in the text.

TABLE (I)

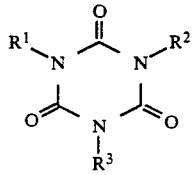

| Example No. | $R^3$ | $R^1$ | $R^2$ | Physical constants |
|---|---|---|---|---|
| 1 | Ph-CH$_2$— | —C(CH$_3$)$_3$ | —C$_2$H$_5$ | Bp 170° C./0.03 mbar |
| 2 | 2-Cl-Ph-CH$_2$— | —C(CH$_3$)$_3$ | —C$_2$H$_5$ | $^1$H-NMR(CDCl$_3$): 7.39m(1H), 7.22(1H) 7.06m(1H), 5.14s(2H), 3.97q(2H; J=7Hz), 1.67s(9H), 1.23t(3H; J=7Hz). |
| 3 | 4-Cl-Ph-CH$_2$— | —C(CH$_3$)$_3$ | —C$_2$H$_5$ | $^1$H-NMR(CDCl$_3$): 7.40d(2H; J=8Hz) 7.27d(2H; J=8Hz), 4.95s(2H), 3.89q(2H; J=7Hz), 1.66s(9H), 1.21t(3H; J=7Hz). |
| 4 | 2,6-Cl$_2$-Ph-CH$_2$— | —C(CH$_3$)$_3$ | —C$_2$H$_5$ | Mp <50° C. |
| 5 | 2,6-Cl$_2$-Ph-CH$_2$— | —CH$_2$—C(CH$_3$)$_3$ | —CH$_3$ | Mp 130° C. |
| 6 | 4-CH$_3$-Ph-CH$_2$— | —C(CH$_3$)$_3$ | —C$_2$H$_5$ | $^1$H-NMR(CDCl$_3$): 7.36d(2H; J=8Hz), 7.13d(2H; J=8Hz), 4.96s(2H), 3.88q(2H; J=7Hz), 2.33s(3H), 1.66s(9H), 1.21t(3H; J=7Hz). |
| 7 | 4-CH$_3$O-Ph-CH$_2$— | —C(CH$_3$)$_3$ | —C$_2$H$_5$ | $^1$H-NMR(CDCl$_3$): 7.42d(2H; J=8Hz), 6.85d(2H; J=8Hz), 4.94s(2H), 3.88q(2H; J=7Hz), 3.79s(3H), 1.65s(9H), 1.20t(3H; J=7Hz). |
| 8 | 4-CF$_3$O-Ph-CH$_2$— | —C(CH$_3$)$_3$ | —C$_2$H$_5$ | $^1$H-NMR(CDCl$_3$): 7.51d(2H; J=8Hz), 7.17d(2H; J=8Hz), 4.99s(2H), 3.90q(2H; J=7Hz), 1.67s(9H), 1.22t(3H; J=7Hz). |
| 9 | 3,4-(CH$_3$)$_2$-Ph-CH(CH$_3$)— | —C(CH$_3$)$_3$ | —CH$_2$—CO—O—C$_2$H$_5$ | Mp 72° C. |
| 10 | 2,5-(CH$_3$)$_2$-Ph-CH(CH$_3$)— | —C(CH$_3$)$_3$ | —C$_2$H$_5$ | oil |
| 11 | 2,4,5-(CH$_3$)$_3$-Ph-CH(CH$_3$)— | —C(CH$_3$)$_3$ | —CH$_2$—C≡CH | Mp 122° C. |
| 12 | indanyl-CH(CH$_3$)— | —C(CH$_3$)$_3$ | —CH$_2$—CH=CH$_2$ | |
| 13 | naphthyl-CH(CH$_3$)— | —C(CH$_3$)$_3$ | —CH$_2$—CN | Mp 152° C. |
| 14 | 3-CH$_3$-4-CH$_3$O-Ph-CH(CH$_3$)— | —C(CH$_3$)$_3$ | —CH$_3$ | |
| 15 | 3,4-(CH$_3$O)$_2$-Ph-CH(CH$_3$)— | —C(CH$_3$)$_3$ | —C$_5$H$_{11}$ | oil |
| 16 | Ph-CH$_2$—CH$_2$— | —C(CH$_3$)$_3$ | —CH$_3$ | Mp 76° C. |
| 17 | Ph-CH$_2$—CH$_2$— | —C(CH$_3$)$_3$ | —C$_2$H$_5$ | Mp 58° C. |
| 18 | Ph-CH$_2$—CH$_2$— | —C(CH$_3$)$_3$ | —CH$_2$—C≡CH | $^1$H-NMR(CDCl$_3$): 7.33–7.19m(5H), 5.85ddt(1H; J=16+10+6Hz), 5.24dq(1H; J=16+1Hz), 5.21dq(1H; J=10+1Hz), 4.42dt(2H; J=6+1Hz), 4.07dd(2H; J=7+6Hz), 3.93dd(2H; J=7+6Hz), 1.61s(9H). |
| 19 | Ph-CH$_2$—CH$_2$— | —C(CH$_3$)$_3$ | —CH$_2$—CH=CH$_2$ | Mp 98° C. |
| 20 | Ph-CH$_2$—CH$_2$— | —C(CH$_3$)$_3$ | —C$_3$H$_7$ | $^1$H-NMR(CDl$_3$): 7.33–7.18m(5H), 4.07dd(2H; J=6+7Hz), 3.77dd(2H; J=6+7Hz), 2.92dd(2H; J=6+7Hz), 1.71–1.51m(2H) 1.63s(9H), 0.92t(3H; J=7Hz). |

TABLE-continued

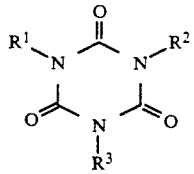
(I)

| Example No. | R³ | R¹ | R² | Physical constants |
|---|---|---|---|---|
| 21 | Ph-CH₂—CH₂— | —C(CH₃)₃ | —CH₂—CO—O—C₂H₅ | Mp 90° C. |
| 22 | Ph-CH(C₂H₅)—CH₂— | —C(CH₃)₃ | —C₂H₅ | ¹H-NMR(CDCl₃): 7.30–7.12m(5H) 4.12dd(1H; J=10+14Hz), 3.93dd(1H; J=7+14Hz), 3.78q(2H; J=7Hz), 3.04ddt(1H; J=7+10+7Hz), 1.71 quint, (2H; J=7Hz), 1.54s(9H), 1.09t(3H; J=7Hz), 0.81t(3H; J=7Hz). |
| 23 | Ph-CH(C₂H₅)—CH₂— | —C(CH₃)₃ | —CH₂—CN | Mp 95° C. |
| 24 | 2-Cl-Ph-CH₂—CH₂— | —C(CH₃)₃ | —C₅H₁₁ | ¹H-NMR(CDCl₃): 7.37–7.10m(4H), 4.15t(2H; J=7Hz), 3.73tbr(2H; J=8Hz), 3.09t(2H; J=7Hz), 1.61s(9H), 1.65–1.47m(2H), 1.35–1.20m(4H), 0.90t(3H; J=7Hz). |
| 25 | 2-Cl-Ph-CH(CH₃)—CH₂— | —C(CH₃)₃ | —C₂H₅ | ¹H-NMR(CDCl₃): 7.40dbr(1H; J=8Hz), 7.30–7.19m(2H), 7.12dt(1H; J=2+8Hz), 4.18–3.83m(3H), 3.79q(2H; J=7Hz), 1.56s(9H), 1.32d(3H; J=7Hz), 1.09t(3H; J=7Hz). |
| 26 | 3-Cl-Ph-CH₂—CH₂— | —C(CH₃)₃ | —C₂H₅ | ¹H-NMR(CDCl₃): 7.28–7.11m(4H), 4.04dd(2H; J=6+7Hz), 3.88q(2H; J=7Hz), 2.90dd(2H; J=6+7Hz), 1.64s(9H), 1.20t(3H; J=7Hz). |
| 27 | 4-Cl-Ph-CH₂—CH₂— | —C(CH₃)₃ | —C₂H₅ | ¹H-NMR(CDCl₃): 7.26d(2H; J=8Hz), 7.17d(2H; J=8Hz), 4.02dd(2H; J=6+7Hz), 3.88q(2H; J=7Hz), 2.89dd(2H; J=6+7Hz), 1.63s(9H), 1.20t(3H; J=7Hz). |
| 28 | 4-Cl-Ph-CH₂—CH₂— | —C(CH₃)₃ | —C₃H₇ | Mp 62° C. |
| 29 | 4-Cl-Ph-CH—CH₂—<br>          \|<br>         CH(CH₃)₂ | —C(CH₃)₃ | —CH₂—C≡CH | ¹H-NMR(CDCl₃): 7.20d(2H; J=8Hz), 7.05d(2H; J=8Hz), 4.47dd(2H; J=2+1Hz), 4.30dd(1H; J=10+12Hz), 4.01dd(1H; J=6+12Hz), 2.92ddd(1H; J=6+8+10Hz), 2.23t(1H; J=2Hz), 1.94d sept. (1H; J=8+7Hz), 1.51s(9H), 1.08d(3H; J=7Hz), 0.74d(3H; J=7Hz), |
| 30 | 2,4-Cl₂-Ph-CH₂—CH₂— | —C(CH₃)₃ | —CH₃ | Mp 86° C. |
| 31 | 2,4-Cl₂-Ph-CH₂—CH₂— | —C(CH₃)₃ | —C₂H₅ | ¹H-NMR(CDCl₃): 7.36t(1H; J=1Hz), 7.17d(2H; J=1Hz), 4.11t(2H; J=7Hz), 3.85q(2H; J=7Hz), 3.06t(2H; J=7Hz), 1.61s(9H), 1.16t(3H; J=7Hz). |
| 32 | 3,4-Cl₂-Ph-CH₂—CH₂— | —C(CH₃)₃ | —C₂H₅ | ¹H-NMR(CDCl₃): 7.37d(1H; J=8Hz), 7.33d(1H; J=2Hz), 7.10dd(1H; J=8+2Hz), 4.03dd(2H; J=6+7Hz), 3.88q(2H; J=7Hz), 2.88dd(2H; J=6+7Hz), 1.64s(9H), 1.19t(3H; J=7Hz). |
| 33 | 3,4-Cl₂-Ph-CH₂—CH₂— | —C(CH₃)₃ | —CH₂—C≡CH | Mp 88° C. |
| 34 | 2,6-Cl₂-Ph-CH₂—CH₂— | —C(CH₃)₃ | —C₂H₅ | Mp 112° C. |
| 35 | 2,6-Cl₂-Ph-CH(CH₃)—CH₂— | —C(CH₃)₃ | —C₂H₅ | Mp 124° C. |
| 36 | 2-CH₃-Ph-CH₂—CH₂— | —C(CH₃)₃ | —C₂H₅ | ¹H-NMR(CDCl₃): 7.19–7.09m(4H), 4.01dd(2H; J=6+7Hz), 3.88q(2H; J=7Hz), 2.93dd(2H; J=6+7Hz), 2.41s((3H), 1.64s(9H), 1.19t(3H; J=7Hz). |
| 37 | 3-CH₃-Ph-CH₂—CH₂— | —C(CH₃)₃ | —C₂H₅ | ¹H-NMR(CDCl₃): 7.20t(1H; J=8Hz), 7.07–7.00m(3H), 4.05dd(2H; J=6+7Hz), 3.88q(2H; J=7Hz), 2.88dd(2H; J=6+7Hz), 2.31s(3H), 1.63s(9H), 1.19t(3H; J=7Hz). |
| 38 | 4-CH₃-Ph-CH₂—CH₂ | —C(CH₃)₃ | —C₂H₅ | Mp 64° C. |
| 39 | 4-CH₃-Ph-CH₂—CH₂— | —C(CH₃)₃ | —CH(CH₃)₂ | ¹H-NMR(CDCl₃): 7.17–7.07m(4H), 4.91 sept. (1H; J=7Hz), 4.01dd(2H; J=6+7Hz), 2.87dd(2H; J=6+7Hz), 2.30s(3H), 1.62s(9H, 1.41d(6H; J=7Hz). |
| 40 | 3-CF₃-Ph-CH₂—CH₂— | —C(CH₃)₃ | —C₂H₅ | Mp 66° C. |
| 41 | 3-CF₃-Ph-CH₂—CH₂— | —C(CH₃)₃ | —CH(CH₃)₂ | ¹H-NMR(CDCl₃): 7.48–7.42m(4H), 4.91 sept, (1H; J=7Hz), 4.07dd(2H; J=6+7Hz), 3.00dd(2H; J=6+7Hz), |

TABLE-continued (I) Structure: R¹-N and R²-N on a 6-membered ring with three C=O groups and R³-N

| Example No. | R³ | R¹ | R² | Physical constants |
|---|---|---|---|---|
| | | | | 1.61s(9H), 1.40d(6H; J=7Hz). |
| 42 | 4-(CH₃)₃C-Ph-CH₂—CH₂— | —C(CH₃)₃ | —CH₃ | ¹H-NMR(DMSO): 7.30d(2H; J=8Hz), 7.11d(2H; J=8Hz), 3.90dd(2H; J=6+7Hz), 3.11s(3H), 2.79dd(2H; J=6+7Hz), 1.52s(9H), 1.25s(9H). |
| 43 | 4-(CH₃)₃C-Ph-CH₂—CH₂— | —C(CH₃)₃ | —C₂H₅ | ¹H-NMR(CDCl₃): 7.32d(2H; J=8Hz), 7.17d(2H; J=8Hz) 4.07dd(2H; J=6+7Hz) 3.88q(2H; J=7Hz), 2.90dd(2H; J=6+7Hz), 1.61s(9H), 1.29s(9H), 1.18t(3H; J=7Hz). |
| 44 | 3,4-(CH₃)₂-Ph-CH₂—CH₂ | —C(CH₃)₃ | —C₂H₅ | ¹H-NMR(CDCl₃): 7.07d(1H; J=8Hz), 7.01d(1H; J=1Hz), 6.98dd(1H; J=8+1Hz), 4.01dd(2H; J=6+7Hz), 3.88q(2H; J=7Hz), 2.86dd(2H; J=6+7Hz), 2.23sbr(6H), 1.65s(9H), 1.19t(3H; J=7Hz). |
| 45 | 2-CH₃O-Ph-CH₂—CH₂— | —C(CH₃)₃ | —C₂H₅ | ¹H-NMR(DMSO): 7.18dt(1H; J=2+8Hz), 7.07dd(1H; J=2+8Hz), 6.91dbr(1H; J=8Hz), 6.84tbr(1H; J=8Hz), 3.97t(2H; J=7Hz), 3.74s(3H), 3.70q(2H; J=7Hz), 2.86t(2H; J=7Hz), 1.52s(9H), 1.06t(3H; J=7Hz), |
| 46 | 3-CH₃O-Ph-CH₂—CH₂— | —C(CH₃)₃ | —C₂H₅ | ¹H-NMR(CDCl₃): 7.21dt(1H; J=2+8Hz), 6.87–6.73m(3H), 4.06dd(2H; J=6+7Hz), 3.88q(2H; J=7Hz), 3.78s(3H), 2.90dd(2H; J=6+7Hz), 1.63s(9H), 1.19t(3H; J=7Hz). |
| 47 | 4-CH₃O-Ph-CH₂—CH₂— | —C(CH₃)₃ | —C₂H₅ | ¹H-NMR(CDCl₃): 7.16d(2H; J=8Hz), 6.83d(2H; J=8Hz) 4.02dd(2H; J=6+7Hz) 3.87q(2H; J=7Hz), 3.78s(3H), 2.87dd(2H; J=6+7Hz), 1.64s(9H), 1.19t(3H; J=7Hz). |
| 48 | 3-Cl-4-CF₃O-Ph-CH₂—CH₂— | —C(CH₃)₃ | —C₂H₅ | ¹H-NMR(CDCl₃): 7.36d(1H; J=2Hz), 7.29–7.14m(2H), 4.05dd(2H; J=7+8Hz), 3.89q(2H; J=7Hz), 2.92dd(2H; J=7+8Hz), 1.63s(9H), 1.19t(3H; J=7Hz). |
| 49 | 2,5-(CH₃O)₂-Ph-CH₂—CH₂— | —C(CH₃)₃ | —C₂H₅ | ¹H-NMR(CDCl₃): 6.78–6.67m(3H), 4.10t(2H; J=7Hz), 3.83t(2H; J=7Hz), 3.77s(3H), 2.91t(2H; J=7Hz), 1.60s(9H), 1.15t(3H; J=7Hz), 3.73s(3H). |
| 50 | 3,4-(CH₃O)₂-Ph-CH₂—CH₂— | —C(CH₃)₃ | —C₂H₅ | ¹H-NMR(DMSO): 6.86d(1H; J=8Hz), 6.74d(1H; J=2Hz), 6.68dd(1H; J=8+2Hz), 3.91dd(2H; J=6+7Hz), 3.71q(2H; J=7Hz), 3.72(3H), 3.70s(3H), 2.77d(2H; J=6+7Hz), 1.54s(9H), 1.07t(3H; J=7Hz). |
| 51 | H₃C—O-Ph(O—CH₂—Ph)-CH₂—CH₂— | —C(CH₃)₃ | —C₂H₅ | ¹H-NMR(CDCl₃): 7.51dd(2H; J=8+2Hz), 7.41–7.29m(4H), 7.00t(1H; J=8Hz), 6.80dt(2H; J=2+8Hz), 5.01s(2H), 4.06t(2H; J=7Hz), 3.85s(3H), 3.75q(2H; J=7Hz), 2.91t(2H; J=7Hz), 1.58s(9H), 1.23t(3H; J=7Hz). |
| 52 | 3-(CH₃O)-Ph-CH(CH₃)CH₂— | —C(CH₃)₃ | —C₂H₅ | ¹H-NMR(CDCl₃): 7.18(1H) 6.75(1H), 6.70(1H), 3.78s(3H), 3.70–4.20m(6H), 2.95–3.12m(1H), 1.55s(9H), 1.11t, (3H; J=7Hz), 0.82t(3H; J=7Hz). |
| 53 | 4-(CH₃O)-Ph-CH[CH₃)₂ ]CH₂— | —CH₂—C(CH₃)₃ | —C₂H₅ | ¹H-NMR(CDCl₃): 7.00d(2H; J=8Hz), 6.75d, (2H; J=8Hz), 4.33dd(1H; J=2Hz+16Hz), 4.05dd(1H; J=6Hz+16Hz), 3.80q(2H; J=7Hz), 3.75s(3H), 3.67s(2H), 2.80–3.00m(1H), 1.85–2.00m(1H), 1.09t(3H; J=7Hz), 0.80s(9H), 0.75d(6H; J=7Hz). |
| 54 | 2,6-Cl₂-Ph-(CH₂)₂CH(CH₃)— | —C(CH₃)₃ | —C₂H₅ | ¹H-NMR(CDCl₃): 7.25(2H) 7.05dd(1H), 4.80–5.00m(1H), 3.88q(2H; J=7Hz), 2.70–3.00m(2H), 2.20–2.42m(1H), 1.90–2.15m(1H), 1.68s(9H), 1.50d(3H; J=7Hz), 1.22t(3H; J=7Hz). |
| 55 | 4-(CH₃O)-Ph-CH[CH(CH₃)₂ ]CH₂— | —C(CH₃)₃ | —C₂H₅ | ¹H-NMR(CDCl₃): 7.05d(2H; J=8Hz), 6.78d |

TABLE-continued (I)

| Example No. | R³ | R¹ | R² | Physical constants |
|---|---|---|---|---|
| | | | | (2H; J=8Hz), 4.38dd(1H; J=2+16Hz), 4.08dd(1H; H=6+16Hz), 3.81q(2H; J=7Hz), 3.69s(3H), 2.80-3.00m(1H), 1.90-2.10m(1H), 1.55s(9H), 1.10t (3H; J=7Hz), 0.75(6H; J=7Hz). |
| 56 | 3-(CH₃O)-Ph-CH[CH(CH₃)₂]CH₂— | —C(CH₃)₃ | —C₂H₅ | ¹H-NMR(CDCl₃): 7.10dt(1H; J=1+5Hz), 6.65-6.70m(2H), 4.31dd(1H; J=2+16Hz), 3.98s(1H; J=16+5Hz), 3.76s(3H), 3.72q (2H; J=7Hz), 2.85-3.00m(1H), 1.85-2.05m(1H), 1.50s(9H), 1.08t(3H; J=7Hz), 0.78d(6H; J=7Hz). |
| 57 | Ph-CH₂—CH₂—CH(CH₃)— | —C(CH₃)₃ | —C₂H₅ | ¹H-NMR(CDCl₃): 7.10-7.30m(5H), 4.75-4.95m (1H), 3.89q(2H; J=7Hz), 2.35-2.80m(3H), 1.90-2.10(1H), 1.65s(9H), 1.43d(3H; J=7Hz), 1.18t(3H; J=7Hz). |
| 58 | 4-(CH₃O)-Ph-CH(CH₃)— | —C(CH₃)₃ | —C₂H₅ | ¹H-NMR(CDCl₃): 7.35d(2H; J=10Hz), 6.85d (2H; J=10Hz), 5.98q(1H; J=80Hz), 3.85q (2H; J=7Hz), 3.78s(3H), 1.82d(3H; J=8Hz), 1.60s(9H), 1.20t(3H; J=7Hz). |
| 59 | Ph-C(CH₃)₂CH₂— | —C(CH₃)₃ | —C₂H₅ | ¹H-NMR(CDCl₃): 7.15-7.45m(5H), 4.05s (2H), 3.85q(2H; J=7Hz), 1.60s(9H), 1.38s(6H), 1.18t(3H; J=7Hz). |
| 60 | 2-Cl-Ph- | —C(CH₃)₃ | —C₂H₅ | ¹H-NMR(CDCl₃): 7.05-7.25m(4H), 4.85tg(1H), 3.85q(2H; J=7Hz), 2.30-2.85m(3H), 1.90-2.10m(1H), 1.65s(9H), 1.45d(3H; J7Hz), 1.22t(3H; J=7Hz). |
| 61 | 4-Cl-Ph-CH₂—CH₂—CH(CH₃)— | —C(CH₃)₃ | —C₂H₅ | ¹H-NMR(CDCl₃): 7.19d(2H); J=9Hz), 7.05d(2H; J=9Hz), 4.83tg(1H), 3.81q(2H; J=7Hz), 2.30-2.70m(3H), 1.90-2.10m(1H), 1.65s(9H), 1.42d(3H, J=8Hz), 1.20t(3H; J=7Hz). |
| 62 | PH-CH₂— | —C(CH₃)₂C≡CH | —CH₃ | ¹H-NMR(CDCl₃): 7.5m(2H, 7.25-7.40m(3H), 5.02s(2H), 3.28s(3H), 2.55s(1H), 1.95s(6H). |
| 63 | Ph-CH₂— | —C(CH₃)₂CH=CH₂ | —C₂H₅ | |
| 64 | Ph-CH₂— | cyclopentyl-CH₃ | —C₂H₅ | Mp 52° C. |
| 65 | 2-Cl-Ph-CH₂—CH₂— | —C(CH₃)₃ | —C₂H₅ | ¹H-NMR(CDCl₃): 7.37-7.30m(1H), 7.24-7.13m(3H), 4.14t(2H; J=7Hz), 3.85q(2H; J=7Hz), 3.09t(2H; J=7Hz), 1.60s(9H), 1.14t(3H; J=7Hz). |
| 66 | 4-Cl-Ph-CH—CH₂—<br>      \|<br>     CH(CH₃)₂ | —C(CH₃)₃ | —C₂H₅ | ¹H-NMR(CDl₃): 7.21d(2H; J=8Hz), 7.04d(2H; J=8Hz), 4.28dd(1H; J=11+13Hz), 3.98dd(1H; J=6+13Hz), 3.75q(2H; J=7Hz), 2.92ddd(1H; J=6+9+11Hz), 1.94d sept.(1H; J=6+7Hz), 1.51s(9H), 1.06t(3H; J=7Hz), 1.08d(3H; J=7Hz), 0.74d(3H; J=7Hz). |

The abbreviations denote:
Bp = boiling point
Mp = melting point
Ph = phenyl ring Preparation of the Hitherto Unknown Urea=Starting Material

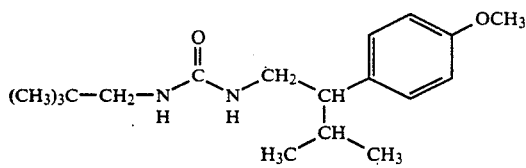

10.5 g (0.054 mol) of 2-(4-methoxyphenyl)-2-(2-propyl)ethylamine are dissolved in 100 ml of absolute toluene, and a solution of 7.3 g (0.065 mol) of neopentyl isocyanate, dissolved in 10 ml of absolute toluene, is added at room temperature. The mixture is refluxed for 15 minutes and allowed to cool, and the precipitate is filtered off with suction. Yield 13.7 g=83% of theory, melting point 132° C.

The other urea derivatives of the formulae (VI) and (VII) can be prepared analogously to this example or to the references cited.

USE EXAMPLES

In the following use examples, the compounds listed below are employed as comparison substances:

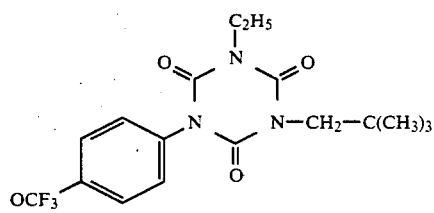

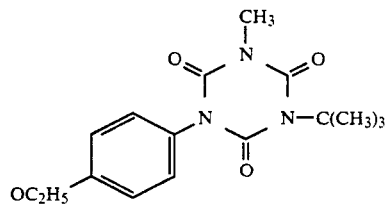

EXAMPLE A

Pyricularia Test (Rice)/Protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown by many of the compounds according to the invention.

EXAMPLE B

Pyricularia Test (Rice)/Systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

At an exemplary application rate of 100 mg of active compound per 100 cm², most of the compounds show a good degree of effectiveness.

It will be understood that the specification and examples are illustrative but not limitative of the present invention and that other embodiments within the spirit and scope of the invention will suggest themselves to those skilled in the art.

What is claimed is:

1. A trisubstituted 1,3,5-triazine-2,4,6-trione of the formula

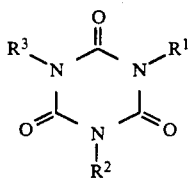

in which
$R^1$, $R^2$ and $R^3$ are different radicals and
$R^1$ represents straight-chain or branched alkyl having 1 to 12 carbon atoms, straight-chain or branched alkenyl having 3 to 12 carbon atoms or straight-chain or branched alkinyl having 3 to 12 carbon atoms, these radicals being optionally monosubstituted to polysubstituted by identical or different substituents from the group consisting of alkoxy having 1 to 4 carbon atoms, halogenoalkoxy having 1 to 3 carbon atoms and 1 to 5 identical or different halogen atoms, alkylthio having 1 to 3 carbon atoms, and halogenoalkylthio having 1 to 3 carbon atoms and 1 to 5 identical or different halogen atoms; or $R^1$ furthermore represents cycloalkyl which has 3 to 8 carbon atoms and which is optionally monosubstituted to hexasubstituted by identical or different substituents from the group consisting of alkyl having 1 to 4 carbon atoms, alkoxy having 1 to 3 carbon atoms, halogenoalkoxy having 1 to 3 carbon atoms and 1 to 5 identical or different halogen atoms, alkylthio having 1 to 3 carbon atoms, and halogenoalkylthio having 1 to 3 carbon atoms and 1 to 5 identical or different halogen atoms, $R^2$ represents alkyl having 1 to 10 carbon atoms, alkenyl having 3 to 10 carbon atoms, alkinyl having 3 to 10 carbon atoms, alkoxyalkyl having 1 to 3 carbon atoms each in the alkoxy moiety and the alkyl moiety, alkylthioalkyl having 1 to 3 carbon atoms each in the alkylthio moiety and the alkyl moiety, alkoxycarbonylalkyl having 1 to 3 carbon atoms in the alkoxy moiety and 2 or 3 carbon atoms in the alkyl moiety, or cyanoalkyl having 1 to 5 carbon atoms in the alkyl moiety, $R^3$ represents aralkyl having 1 to 12 carbon atoms in the straight-chain or branched alkyl moiety and 6 to 12 carbon atoms in the aryl moiety, the aryl radical being optionally monosubstituted to pentasubstituted by identical or different substituents from the group consisting of halogen, alkyl having 1 to 6 carbon atoms, halogenoalkyl having 1 to 4 carbon atoms and 1 to 5 identical or different halogen atoms, alkoxy having 1 to 4 carbon atoms, halogenoalkoxy having 1 to 4 carbon atoms and 1 to 5 identical or different halogen atoms, alkylthio having 1 to 4 carbon atoms, halogenoalkylthio having 1 to 4 carbon atoms and 1 to 5 identical or different halogen atoms, monoalkylamino or dialkylamino which have optionally identical or different, straight-chain or branched alkyl radicals each having 1 to 4 carbon atoms, nitro and benzyloxy, or the aryl radical optionally carries a fused, saturated ring having 3 to 5 carbon atoms.

2. A trisubstituted 1,3,5-triazine-2,4,6-trione according to claim 1, in which $R^1$, $R^2$ and $R^3$ are different radicals and $R^1$ represents straight-chain or branched alkyl having 1 to 10 carbon atoms, straight-chain or branched alkenyl having 3 to 8 carbon atoms or straight-chain or branched alkinyl having 3 to 8 carbon atoms, these radicals being in each case optionally monosubstituted to trisubstituted by identical or different substituents from the group consisting of alkoxy having 1 to 3 carbon atoms, halogenoalkoxy having 1 or 2 carbon atoms and 1 to 3 chlorine and/or fluorine atoms, alkylthio having 1 or 2 carbon atoms, and halogenoalkylthio having 1 or 2 carbon atoms and 1 to 3 chlorine plus fluorine atoms; or $R^1$ furthermore represents cycloalkyl which has 3 to 6 carbon atoms and which is optionally monosubstituted to hexasubstituted by identical or different substituents from the group consisting of fluorine, chlorine, alkyl having 1 to 3 carbon atoms, alkoxy having 1 or 2 carbon atoms, halogenoalkoxy having 1 or 2 carbon atoms and 1 to 5 chlorine and fluorine atoms, alkylthio having 1 or 2 carbon atoms, and halogenoalkylthio having 1 or 2 carbon atoms and 1 to 3 chlorine plus fluorine atoms, $R^2$ represents alkyl having 1 to 8 carbon atoms, alkenyl having 3 to 8 carbon atoms, alkinyl having 3 to 8 carbon atoms, alkoxyalkyl having 1 or 2 carbon atoms in the alkoxy moiety and 1 to 3 carbon atoms in the alkyl moiety, alkylthioalkyl having 1 or 2 carbon atoms in the alkylthio moiety and 1 to 3 carbon atoms in the alkyl moiety, alkoxycarbonylalkyl having 1 or 2 carbon atoms in the alkoxy moiety and 2 or 3 carbon atoms in the alkyl moiety, or cyanoalkyl having 1 to 3 carbon atoms in the alkyl moiety, and $R^3$ represents aralkyl having 1 to 5 carbon atoms in the straight-chain or branched alkyl moiety and aryl represents phenyl or naphthyl, each of which can optionally be monosubstituted to tetrasubstituted by identical or different substituents from the group consisting of fluorine, chlorine, bromine, alkyl having 1 to 5 carbon atoms, halogenoalkyl having 1 or 2 carbon atoms and 1 to 5 chlorine plus fluorine atoms, alkoxy having 1 to 3 carbon atoms, halogenoalkoxy having 1 or 2 carbon atoms and 1 to 5 chlorine plus fluorine atoms, alkylthio having 1 or 2 carbon atoms, halogenoalkylthio having 1 or 2 carbon atoms and 1 to 5 chlorine plus fluorine atoms, dialkylamino having identical or different, straight-chain or branched alkyl radicals each having 1 to 3 carbon atoms, nitro and benzyloxy, or the phenyl ring contains a tri- or tetramethylene chain in the 1,2-position.

3. A trisubstituted 1,3,5-triazine-2,4,6-trione according to claim 1, in which $R^1$, $R^2$ and $R^3$ are different radicals and $R^1$ represents straight-chain or branched alkyl having 1 to 8 carbon atoms, straight-chain or branched alkenyl having 3 to 6 carbon atoms or straight-chain or branched alkinyl having 3 to 6 carbon atoms, it being possible for these radicals to be monosubstituted to trisubstituted by identical or different substituents from the group consisting of alkoxy having 1 or 2 carbon atoms, and alkylthio having 1 or 2 carbon atoms; or $R^1$ furthermore represents cycloalkyl which has 3 to 6 carbon atoms and which can optionally be monosubstituted to trisubstituted by identical or different substituents from the group consisting of fluorine, chlorine, methyl, ethyl, methoxy, ethoxy, methylthio, ethylthio and trifluoromethyl, $R^2$ represents methyl, ethyl, propyl, n-, sec.-, iso-, tert.-butyl, n-pentyl, iso-pentyl, neo-pentyl, tert.-pentyl, allyl, 2-butenyl, propargyl, 2-butinyl, methoxymethyl, ethoxymethyl, methylthiomethyl, methoxycarbonylmethyl, ethoxycarbonylmethyl, methoxycarbonylethyl, cyanomethyl or cyanoethyl, and $R^3$ represents aralkyl having 1 to 7 carbon atoms in the straight-chain or branched alkyl radical and aryl represents phenyl or naphthyl each of which can be monosubstituted to trisubstituted by identical or different substituents from the group consisting or fluorine, chlorine, alkyl having 1 to 4 carbon atoms, halogenoalkyl having 1 or 2 carbon atoms and 1 to 5 chlorine plus fluorine atoms, alkoxy having 1 or 2 carbon atoms, halogenoalkoxy having 1 or 2 carbon atoms and 1 to 5 chlorine plus fluorine atoms or benzyloxy, or the phenyl ring carries a trimethylene chain in the 1,2-position.

4. A compound according to claim 1, wherein such compound is 1-tert.-butyl-5-ethyl-3-[2-(3-methoxyphenyl)propyl]-1,3,5-triazine-2,4,6-trione of the formula 5. A compound according to claim 1, wherein such compound is 1-tert.-butyl-5-ethyl-3-(1-methyl-3-phenyl-propyl)-1,3,5-triazine-2,4,6-trione of the formula

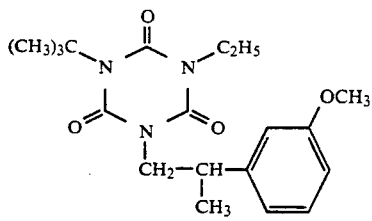

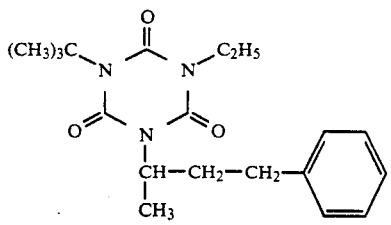

6. A fungicidal composition comprising a fungicidally effective amount of a compound according to claim 1 and a diluent.

7. A method of combating fungi which comprises applying to such fungi or to a fungus habitat a fungicidally effective amount of a compound according to claim 1.

8. The method according to claim 7, wherein such compound is
1-tert.-butyl-5-ethyl-3-[2-(3-methoxyphenyl)propyl]-1,3,5-triazine-2,4,6-trione or
1-tert.-butyl-5-ethyl-3-(1-methyl-3-phenyl-propyl)-1,3,5-triazine-2,4,6-trione.

* * * * *

UNITED STATES PATENT AND TRADEMARK OFFICE
CERTIFICATE OF CORRECTION

PATENT NO. : 5,077,291

DATED : December 31, 1991

INVENTOR(S) : Uhr et al.

It is certified that error appears in the above-identified patent and that said Letters Patent is hereby corrected as shown below:

Col. 22, line 56   Delete " or " and substitute -- of --.

Signed and Sealed this

Sixth Day of July, 1993

Attest:

MICHAEL K. KIRK

Attesting Officer

Acting Commissioner of Patents and Trademarks